United States Patent [19]

Miller et al.

[11] Patent Number: 4,591,614
[45] Date of Patent: May 27, 1986

[54] PREPARATION OF OLIGODEOXYRIBONUCLEOSIDE ALKYL OR ARYLPHOSPHONATES

[75] Inventors: Paul S. Miller, Baltimore; Paul O. P. T'so, Lutherville, both of Md.

[73] Assignee: The Johns Hopkins University, Baltimore, Md.

[21] Appl. No.: 605,451

[22] Filed: Apr. 30, 1984

Related U.S. Application Data

[63] Continuation-in-part of Ser. No. 540,185, Oct. 7, 1983, Pat. No. 4,507,433.

[51] Int. Cl.$^4$ .................. C07H 19/10; C07H 21/02; C07H 21/04
[52] U.S. Cl. .................. 525/54.11; 536/27; 536/28; 536/29; 514/7; 514/76
[58] Field of Search .................. 525/54.11; 536/27, 28, 536/29; 424/180; 514/2, 7, 76, 103

[56] References Cited

U.S. PATENT DOCUMENTS 4,401,796 8/1983 Itakura .................. 536/28
4,458,066 7/1984 Caruthers et al. .................. 536/28

Primary Examiner—John Kight
Assistant Examiner—Nathan M. Nutter
Attorney, Agent, or Firm—Cushman, Darby & Cushman

[57] ABSTRACT

Oligonucleoside-3'-alkyl or aryl phosphonates are prepared by condensing (i) a 5'-protected nucleoside 3'-alkyl or aryl phosphonic imidazolide with (ii) a nucleoside or oligomer which is attached through its 3'-position to a polymer support. The process is advantageously carried out in the presence of tetrazole.

14 Claims, 2 Drawing Figures

PREPARATION OF OLIGODEOXYRIBONUCLEOSIDE ALKYL OR ARYLPHOSPHONATES

The work disclosed herein was supported in part by a grant from the National Institute of Health.

RELATED APPLICATIONS

The present application is a continuation-in-part of Ser. No. 540,185, now U.S. Pat. No. 4,507,433 filed Oct. 7, 1983, the contents of which are incorporated herein by reference.

The present invention is concerned with certain improvements in the preparation of deoxyribonucleoside alkyl or arylphosphonates and oligomers thereof.

Novel and useful oligodeoxyribonucleoside methylphosphonates are described in our U.S. application Ser. No 206,297, filed Nov. 12, 1980 now U.S. Pat. No. 4,469,863. Further uses of such oligonucleotides are also disclosed in our U.S. application Ser. No. 363,230, filed Mar. 28, 1982. The disclosures of these two applications are also incorporated herein by reference.

The instant invention is concerned, inter alia, with improved methods for preparing oligodeoxyribonucleoside alkyl or arylphosphonates, e.g. the methylphosphonates, disclosed in U.S. Pat. No. 4,469,863 and Ser. No. 363,230, and related products.

BACKGROUND OF THE INVENTION

Oligonucleoside methylphosphonates have been used to study the function of specific RNA sequences in biochemical and intact cellular systems. See Miller et al, Biochemistry 20, 1874–1880 (1981) and Jayaraman et al, Proc. Nat'l Acad. Sci. 78, 1537–1541 (1981). Since these nonionic nucleic acid analogs can be taken up intact by mammalian cells and certain bacterial cells in culture, these compounds promise to be useful reagents for exploring and regulating the function of nucleic acids within living cells. See, in this regard, the above-mentioned U.S. application Ser. No. 363,230 and U.S. Pat. No. 4,469,863.

Various procedures have previously been described for synthesizing oligonucleoside methylphosphonates and the like. Thus, the synthesis of oligonucleoside methylphosphonates on a silica gel support has previously been described (Miller et al (1983) Nucleic Acids Res., 11, 5189–5204). In that work, protected nucleoside 3'-methyl-phosphonic chlorides or tetrazolides were used as synthetic intermediates. While oligothymidine methylphosphonates could be efficiently synthesized by this procedure, low yields were encountered when other nucleosides, particularly d-[(MeO)₂Tr]ibuG, were used.

The preparation of oligonucleoside methylphosphonates on a glass support using nucleoside 3'-methylphosphine chlorides as reactive intermediates has also been described (Sinha et al, Tetrahedron Letters, 24, 877–880, 1983).

In U.S. Pat. No. 4,507,433, we have described an improved method for synthesizing oligodeoxyribonucleoside alkyl or arylphosphonates, notably methylphosphonates, of preselected sequence and length in high yield which comprises condensing (1) a 5'-protected nucleoside 3'-alkyl or arylphosphonate alkylammonium salt with (2) a nucleoside or oligomer thereof bound to a solid or insoluble polymer support, e.g. a crosslinked polystyrene support. The condensation can be repeated as many times as necessary, with the same nucleoside (1) or a different one, and using the previously obtained oligomer product after deprotecting the 5-position as reactant (2), to ultimately obtain an oligonucleoside phosphonate having the desired sequence and length. Typically the invention may be used to prepare an oligomer containing up to nine nucleoside units or even more.

The invention of U.S. Pat. No. 4,507,433 also includes convenient means, notably the use of a diamino alkane, preferably ethylene diamine dissolved in ethanol, for cleaving the oligomer product from the supporting polymer.

BRIEF DESCRIPTION OF THE INVENTION

The present invention is based, at least in part, on the finding that oligonucleoside-3'-alkyl or aryl phosphonates can be prepared in high yield by condensing (i) a 5'-protected nucleoside 3'-alkyl or aryl phosphonic imidazolide or other azole derivative, e.g. triazole or tetrazole, with (ii) a nucleoside or oligomer thereof which is attached through its 3'-position to a polymer support, e.g. polystyrene. The condensation can be repeated any number of times by deprotecting the 5'-position of the oligomer product of the preceding condensation and using this as component (ii) for further condensation, the condensation being repeated as many times as appropriate to obtain the desired oligomer.

Preferably the condensation is carried out in the presence of tetrazole or equivalent azole, e.g. triazole or nitrotriazole, as catalyst.

Component (i) is advantageously synthesized by reacting a 5'-protected nucleoside with an appropriate alkyl or aryl phosphonic-bisimidazolide. Thus, for example, protected 5'-dimethoxytritylribonucleoside-3-methylphosphonic imidazolides, d-[(MeO)₂Tr]NpIm, can be readily synthesized by reaction of the 5'-protected nucleoside with methylphosphonic-bisimidazolide in acetonitrile solution. The resulting imidazolides are stable for at least eight weeks in this solution when stored at −20° C. and can be used as component (i) to prepare oligonucleoside methylphosphonates or the like on a 1% crosslinked polystyrene support. Reaction of the d-[(MeO)₂Tr]NpIm with, for example, thymidine linked to polystyrene to yield the protected dimer has been found to proceed to approximately 95% completion after six hours with no detectable formation of side products. Addition of tetrazole accelerates the reaction which yields dimers in greater than 90% yield within one hour. The indicated coupling conditions can be used in stepwise fashion to synthesize oligomers of the type d-Np(Np)nN where n is, for example, an integer up to 10, advantageously 6–10. The coupling reactions proceed in good yield with essentially no side product formation. Hence the deprotected oligomers can be easily purified by a one step ion exchange chromatography procedure.

DETAILED DESCRIPTION

Figure 1:
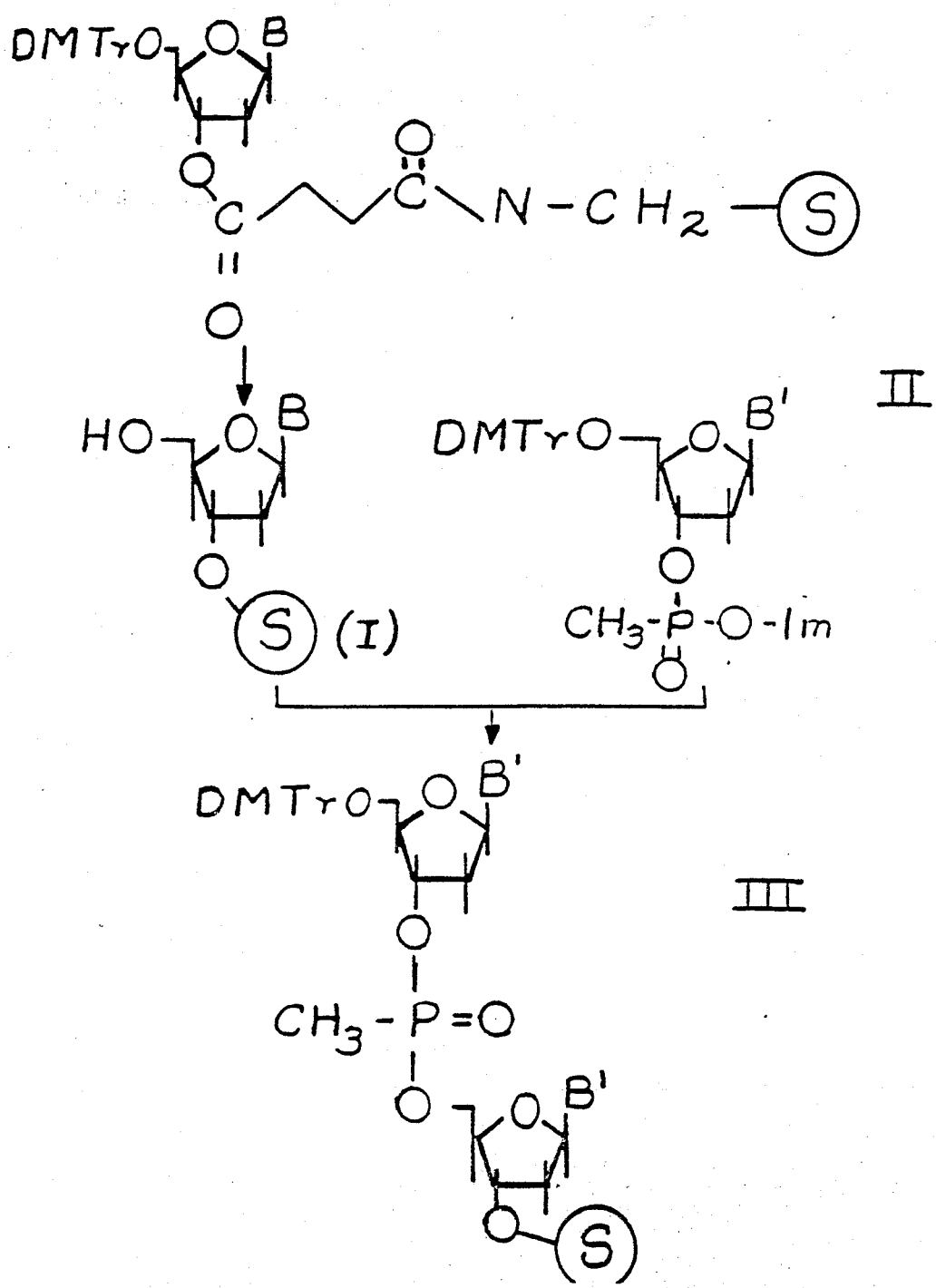
FIG. 1 illustrates the removal of the protecting group (DMTr) on a nucleoside or oligonucleoside bound to polystyrene (s) to provide a polymer bound reactant (I) and then condensing (I) with a 5'-protected nucleoside methylphosphonic imidazolide (II) to obtain the desired oligodeoxynucleoside product (III).

The invention is hereinafter described by reference to the solid phase synthesis of oligonucleoside methyl phosphonates using 5'-protected nucleoside-3'-methylphosphonic imidazolides for condensation with a nucleoside bound via its 3'-position to a polystyrene support, notably a crosslinked polystyrene support. A 5'-protecting group used herein for purposes of illustrating the invention is dimethoxytrityl (DMTr). Other protecting groups (e.g. benzoyl or isobutyl) are also used to protect the base portion of the nucleoside throughout the process for preparing the desired product. It will be recognized, however, that other protecting groups than dimethoxytrityl and the indicated base protecting groups may be used. Additionally alkyl or aryl phosphonates in addition to the exemplified methyl phosphonates, for example, those wherein the alkyl contains up to 6 carbons or the aryl is phenyl or naphthyl, are contemplated herein. Other modifications will also be evident to those in the art.

The invention contemplates the use of any polymer support which is insoluble in the reaction medium and to which the nucleoside can be removably linked. Polystyrene is the preferred support, particularly if it includes a degree of cross-linking, for example, in the order of 1–5% by weight.

A unique advantage of the present process is that the condensation cycle, separation from the support and removal of base protecting groups and purification can be carried out in the same vessel thus obviating the need for transferring the product from one vessel to another for processing.

The process of the invention may be used for the synthesis of two types of oligomers, namely, those containing only methylphosphonate linkages, d-Np(Np)$_n$N, and those which terminate with a 5' nucleotide residue d-Np(Np)$_n$N. According to the invention an advantage of the latter oligomers is that they can be phosphorylated by polynucleotide kinase, and may be separated by polyacrylamide gel electrophoresis according to their chain length. This is useful in characterizing the product. While d-Np(Np)$_n$N serve as substrates for both polynucleotide kinase and reverse transcriptase, d-Np(Np)$_n$N are not phosphorylated by polynucleotide kinase.

Representative of the invention is the preparation of the octamer, d-CpApTpTpCpTpGpT, which has been obtained in 48% isolated yield. The 5'—OH of the octamer can be phosphorylated using T-4 polynucleotide phosphorylase and the resulting oligomer purified by polyacrylamide gel electrophoresis (PAGE). Piperidine randomly cleaves -p- linkages to give a series of shorter oligomers whose number corresponds to the oligomer chain length. Modified Maxam/Gilbert base-specific cleavage reactions followed by PAGE allow determination of the sequence of the oligomer. The results obtained demonstrate that oligonucleoside methylphosphonates can be synthesized in high yield using the process of the invention and can be characterized by procedures similar to those used for oligonucleoside phosphodiesters.

One preferred way of practicing the present invention is illustrated in FIG. 1. The process there exemplified comprises (a) removing the protecting group (DMTr) on a nucleoside or oligonucleoside bound to crosslinked or crosslinkable polystyrene (S) to provide the polymer bound reactant (I); and (b) condensing reactant (I) through its now deprotected 5'—OH group with a 5'-protected nucleoside methylphosphonic imidazolide (II) to obtain the desired oligodeoxynucleoside product (III). The reference letters B and B' represent simplified designations of protected pyrimidine or purine bases as conventional in DNA nucleosides. As is known in the art, each DNA nucleoside is composed of a purine or pyrimidine base joined to deoxyribose sugar. The DNA bases include adenine, guanine, cytosine and thymine which are generally represented by the letters A, G, C and T, respectively. The first two of these are purine bases while the last two (C and T) are pyrimidine bases.

In using the present invention, the reactant nucleosides will be selected to provide the desired base sequence in the oligonucleoside product, it being understood, from the foregoing, that condensation between product (III) and a nucleoside (II), with appropriate choice of bases (B) and (B'), may be repeated a number of times to give a final product (III') having the desired oligomer length and sequence. As noted earlier, oligomers comprising up to ten, and possibly even more, nucleoside methylphosphonate units may be prepared in this way.

According to the process shown in FIG. 1, the 5'-DMTr protected nucleoside is bound via its 3'-position to the support, advantageously an aminomethyl succinyl-derivatized polystyrene support. The 5'-protecting group is removed by using, for example, 1 M zinc bromide solution. The deprotected nucleoside is then condensed with the DMTr protected nucleoside 3'-methylphosphonic imidazolide. The condensation, as shown in FIG. 1, is preferably carried out in the presence of tetrazole as catalyst.

In the process disclosed in U.S. Pat. No. 4,507,433, mesitylenesulfonyl-3-nitrotriazole (MSNT) is used as the catalyst or condensing agent to facilitate the condensation between the 5'-protected nucleoside-3'-methylphosphonate triethyl ammonium salt and the supported nucleoside. However, it has been found that in some cases the MSNT can potentially lead to the formation of undesired side products, particularly those resulting from sulfonylation of nucleoside or oligomer 5'-hydroxyl groups. These side reactions lower the overall yield and complicate purification of the desired product.

According to the present invention, it has been found that use of the 5'-protected imidazolide reactants (i), e.g. 5'-dimethoxytrityldeoxyribonucleoside-3'-methylphosphonic imidazolides, d-[(MeO)$_2$Tr]NpIm, in the presence of tetrazole can be used to synthesize the oligonucleoside methylphosphonates on a polystyrene support in good overall yield with little, if any, side reactions. Since side reactions are greatly reduced or totally eliminated by use of this reagent, the desired methylphosphonate oligomer can be purified by a simple, one step procedure.

Materials for use in carrying out the present process are commercially available or may be readily prepared. For example, protected nucleosides, d-[(MeO)$_2$Tr]N; polystyrene (1% crosslinked and derivatized with d-[(MeO)$_2$Tr]N) and imidazole are commercially available. The same is true for tetrazole which can also be prepared according to available literature.

The invention is illustrated by the following examples:

EXAMPLE 1

Preparation of 5-0-Dimethoxytrityldeoxyribonucleoside-3'-O-Methyl Phosphonic Imidazolides The following operations and reactions were carried out at room temperature in 3 ml or 5 ml V-vials fitted with Teflon-faced silicone septum caps. Imidazole and the protected nucleosides were dried in the reaction vials under vacuum in the presence of $P_2O_5$ overnight and were stored under dry argon. All solutions were transferred via predried gas tight Hamilton syringes having fixed needles. For the preparation of methylphosphonic-bis-imidazolide, liquid methylphosphonic dichloride (1 mmol) was added dropwise to a stirred solution of imidazole (5 mmol) dissolved in 1.1 ml of anhydrous acetonitrile. The solution was briefly vortexed and kept for 10 min. The reaction mixture was then centrifuged to pellet the insoluble imidazole hydrochloride and the supernatant was transferred to a 5 ml V-vial containing a magnetic spin vane. A solution of 5'-dimethoxytrityldeoxyribonucleoside (1.3 mmol) in anhydrous pyridine (0.7 ml) and acetonitrile (0.4 ml) was added dropwise to the stirred methylphosphonic-bis-imidazolide solution over a period of 2 hrs. Stirring was continued overnight at room temperature.

Figure 2:
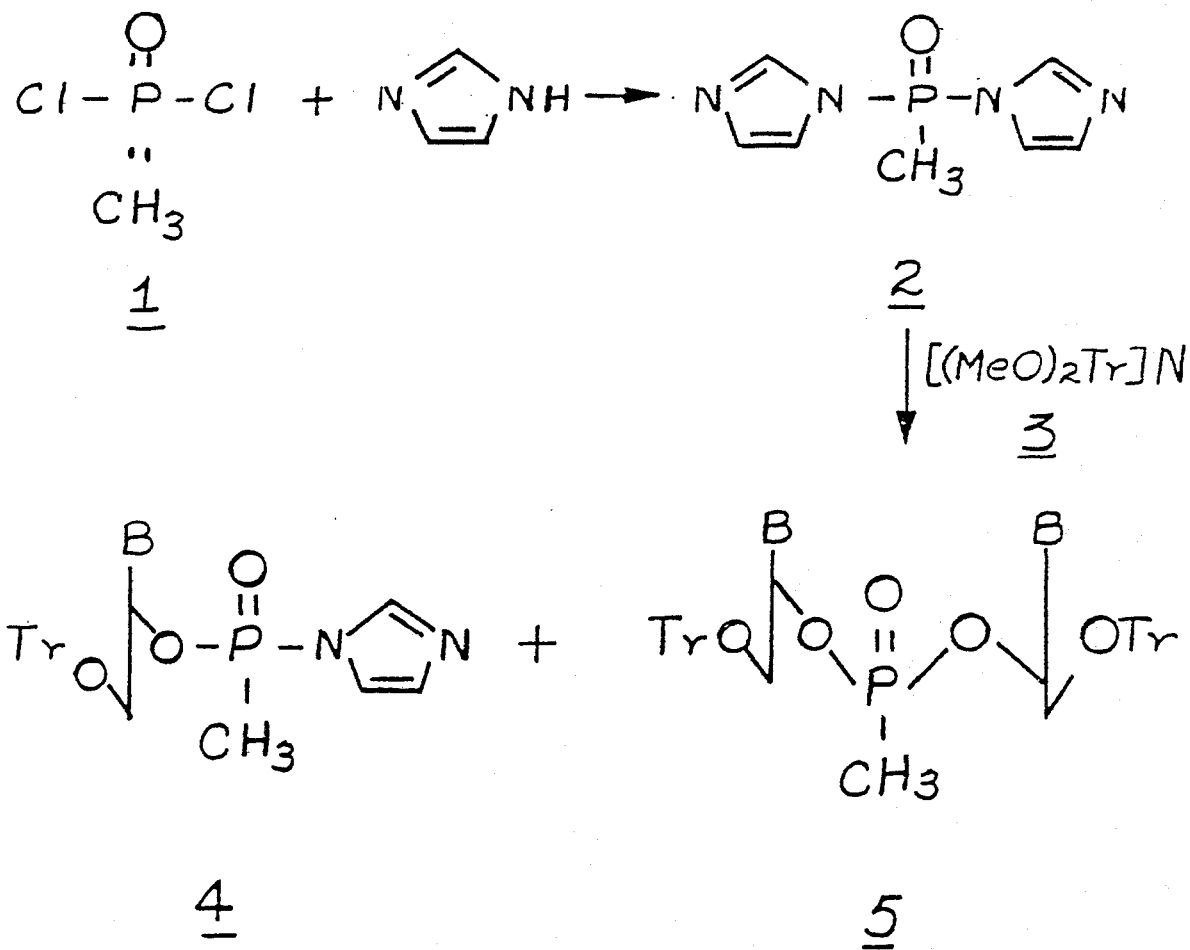
FIG. 2, illustrates the formation of the 5' protectd nucleoside from a methyl phosphonic dichloride and imidazole reaction product with the starting nucleoside, and the appearance of trityl-containing compounds.

The progress of the reaction, which is illustrated in FIG. 2, was monitored by silica gel thin layer chromatography (TLC). A 5 ml aliquot of the reaction mixture was added to a solution containing tetrahydrofuran, triethylamine, water (90:5:5 V/V) and the solvents were evaporated. TLC in 10% methanol-chloroform (V/V) showed the disappearance of the starting nucleoside identified as (3) in FIG. 2, and the appearance of two new trityl-containing compounds identified as (4) and (5) in FIG. 2. A spot at the origin corresponds to 5'-O-di-methoxytritydeoxynucleoside3'-O-methylphosphonic acid which is presumably formed via hydrolysis of d-[(MeO)$_2$Tr]NpIm, the desired product. The other spot whose mobility is slightly faster than the starting nucleoside corresponds to the 3'-3' dimer (5) (see FIG. 2).

The reaction vial was placed in a dessicator jar containing drierite and stored at $-20°$ C. When stored in this way the protected nucleoside-3'-O-methylphosphonic imidazolides are stable for at least 8 weeks as shown by $^{31}P$ nmr spectroscopy and by the ability of the stored reagent to form dinucleoside methylphosphonates.

EXAMPLE 2

Preparation of Dinucleoside Methylphosphonates

5-O-Dimethoxytrityl thymidine derivatized to 1% crosslinked polystyrene (20 mg; 50 μmole/g support) was placed in a sintered glass funnel. The support was treated as described in Table I, steps (1) through (n). The support was transferred to a 1 ml V-vial and was coevaporated with 120 μl of anhydrous pyridine in a vacuum bottle which contained phosphorous pentoxide. A solution of d-[MeO)$_2$Tr]NpIm (100 μl) was added to 16.3 mg of dry tetrazole in a 1 ml V-vial. After 10 min. the solution was transferred to the dry support and the coupling reaction was carried out for 60 min. The support was then transferred to a sintered glass funnel, washed with pyridine (3×2 ml) and ether (3×2 ml) and then dried under vacuum.

The support (1 mg) was treated with 0.2 ml of a solution containing ethylene diamine, ethanol (1:1 V/V) for 3 hours at 65° C. The support was removed and the solvents were evaporated. The residue was treated with 80% acetic acid in water for 1 hr. at room temperature. The solvents were evaporated and the deprotected dimers were analyzed by reversed phase HPLC using a 50 ml linear gradient of 0% to 25% acetonitrile in water at a flow rate of 2.5 ml/min. The dimers which appeared as two peaks due to separation of the two diastereoisomers had the same chromatographic mobilities as those of dimers previously prepared on a silica gel polymer support (Miller et al, 1983, Nucleic Acids Research 11, 5189–5204).

The kinetics of the coupling reaction were determined by stopping the coupling reaction after various periods of time. The products of the reaction were then cleaved from the support and analyzed by HPLC as described above.

EXAMPLE 3

Synthesis of Oligonucleoside Methylphosponates

All operations and reactions were carried out in a 4 ml polypropylene Bio Rad Econocolumn fitted with a three-way Teflon valve and a rubber septum cap as previously described. The appropriate polystyrene support (70 mg) was placed in the column and the operations described in Table I were carried out. The co-evaporation step (step 8) was carried out by adding anhydrous pyridine to the support and transferring the column to a vacuum bottle (Labconco) containing phosphorous pentoxide. A 4 cm drying tube, made from a 1 ml syringe barrel and filled with Drierite was fitted to one of the ports of the three-way valve. The other port was sealed with Parafilm. The valve was opened and the vacuum was quickly applied. The column was kept under vacuum for 60 min. to dry the support. The vacuum was then released by admitting dry argon into the vacuum bottle.

The coupling mixture was prepared by adding 350 μl of d-[(MeO)$_2$Tr]NpIm solution prepared as described above to 57 mg of dry tetrazole in a 1 ml V-vial. After 10 min. the solution was added dropwise to the support and the reaction column was then kept in a dessicator for 1 hr.

In the final coupling step 51 mg of mesitylenesulfonyl-3-nitrotriazole was dissolved in 290 μl of anhydrous pyridine and the solution was transferred to a 1 ml V-vial containing dry d-[(MeO)$_2$Tr]N$_p$.Et$_3$NH. The mixture was vortexed and the coupling solution was added to the dry support. The condensation reaction was carried out for 1.5 to 2 hrs. The support was then washed with pyridine (3×2 ml), methylene chloride/isopropanol solution (3×2 ml) and diethyl ether (3×2 ml), after which it was dried under vacuum.

The protecting groups were removed by sequential treatment with 2 ml of 0.017 M tetra-n-butyl ammonium fluoride in tetrahydrofuran/pyridine/water (8:1:1 V/V) for 40 hrs. 0.5 to 1 ml of ethylenediamine in ethanol (1:1 V/V) for 7 hrs. and 1 ml of 80% acetic acid in water for 75 min. as previously described (Miller et al, 1983, Nucleic Acid Research, 11, 6225–6242). It is essential to completely remove all the ethylenediamine before the acetic acid treatment. This can be accomplished by repeated coevaporation with 95% ethanol.

Following the acetic acid treatment, the solvents were evaporated and the residue was repeatedly co-evaporated with 50% ethanol in water. The residue was then dissolved in 1 ml of water and the solution was extracted with 3, 1 ml portions of ether. Residual ether was removed by evaporation and the solution was diluted to approximately 20 ml with water.

The solution was passed through a DEAE cellulose column (2.5×8 cm) in the bicarbonate form which had been prequilibrated with water. The column was monitored at 254 nm. After the sample was loaded, the column was washed with water until the recorder pen returned to the baseline. The desired oligonucleoside methyl phosphonate was then eluted with 0.15 M triethylammonium bicarbonate. The buffer was removed by coevaporation with water and the oligomer was obtained by lyophilization from water. The purity of the oligomer was checked by C-18 reversed phase HPLC using a 50 ml gradient of 0% to 30% acetonitride in 0.1 M ammonium acetate buffer (pH 5.8) at a flow rate of 2.5 ml per minute. Occasionally an additional peak is observed in the HPLC with a retention time of 3 min. This may be removed by passing the oligomer through a Bio Gel P-2 column (1.2×18 cm). The unwanted material elutes after the oligomer.

DISCUSSION

The foregoing examples show that 5'-O-dimethoxytrityldeoxynucleoside-3'-O-methylphosphonic imidazolides were readily prepared by the two-step procedure outlined in FIG. 2. The bifunctional phosphonylating/condensing agent, methylphosphonic-bis-imidazolide (2) was first prepared in anhydrous acetonitrile solution by reaction of one equivalent of methylphosphonic dichloride (1) with five equivalents of imidazole. This reaction was quantitative as shown by $^{31}$p nmr spectroscopy. After removal of imidazole hydrochloride, the solution of imidazolide (2) was slowly reacted with 1.3 equivalents of protected 5'-dimethoxytrityldeoxynucleoside (3). The use of excess nucleoside ensures complete reaction. This is important since coupling reactions on the polymer support require an excess of the incoming activated nucleoside methylphosphonate. Even trace amounts of unreacted methylphosphonic-bis-imidazolide (2) could lead to unwanted phosphonylation of support-bound nucleosides or oligomers.

The phosphonylation reaction was allowed to proceed at room temperature overnight. When an aliquot of the reaction mixture was examined by TLC after quenching in water, two new products were observed in addition to traces of the starting nucleoside: protected 5'-O-dimethoxytrityldeoxynucleoside-3'-O-methylphosphonic acid which is formed from hydrolysis and the fully protected 3'-3' linked dinucleoside methylphosphonate (5) which forms by reaction of excess nucleoside with (4). A $^{31}$P nmr spectrum of the reaction mixture showed complete disappearance of the resonance at 20.86 ppm corresponding to the bis-imidazole (2) as well as the appearance of resonances corresponding to d-[(MeO)$_2$Tr]NpIm (4) and 3'-3' linked dimer (5). Two $^{31}$P resonances corresponding to the two diastereoisomers of (4) were observed except in the reaction involving the deoxyguanosine derivative. The $^{31}$P resonance of the 3'-3' linked dimer (5) appeared as a singlet. When water was added to the reaction mixture containing the deoxyguanosine derivative of (4), the $^{31}$P resonance of (4) immediately disappeared and was replaced by a resonance at 25.08 ppm which was identical to the $^{31}$P resonance of authentic 5'-O-dimethoxy trityl-N-isobutyldeoxyquanosine-3'-O-methyl phosphonic acid, d-[(MeO)$_2$Tr]ibuGp.

The only other components in the reaction mixture were traces of unreacted nucleoside and 3'-3'-dimer (5). Therefore no further purification of (4) was required, since these side products are inert in the subsequent coupling reaction on the polymer support. The protected 5'-dimethoxytrityldeoxynucleoside-3-methylphosphonic imidazolides are stable in the reaction solution and can be stored as such at −20° C. for at least eight weeks without decomposition or loss of coupling activity as evidenced by $^{31}$P nmr and by the ability of the stored reagent to form dinucleoside methylphosphonate.

The protected nucleoside-3'-methylphosphonic imidazolides in acetonitrile-pyridine solution react slowly with thymidine linked via an aminomethylsuccinyl spacer to 1% crosslinked polystyrene. The formation of the dimer, d-[(MeO)$_2$Tr]TpT was monitored by C-18 reversed phase HPLC. The coupling reaction was approximately 90% complete after 6 hrs. No side products were detected in this reaction. This result confirms the previous nmr observation that no unreacted methylphosphonic-bis-imidazolide (2) remains in the solution of (4) after reaction with (3) as shown in FIG. 2.

When six equivalents of tetrazole were added to a solution of one equivalent of (4), the rate of the coupling reaction increased approximately 6-fold. The reaction was nearly complete after 1 hr. as shown by HPLC. Similar results were obtained with the other three nucleoside methyl-phosphonic imidazoles (Table II). In contrast neither N-methylimidazole nor N,N-dimethyl amino pyridine increase the rate of the coupling reaction. It is not clear how or why the tetrazole functions to increase the rate of the coupling reaction. However, it may protonate the imidazole group thereby making it a better leaving group toward displacement by the nucleoside-5'-OH group. Alternatively the tetrazole may displace the imidazolo group to form a more reactive nucleoside-3'-methylphosphonic tetrazolide intermediate.

The high yields and lack of side products, indicate that the nucleoside-3'-methylphosphonic imidazolides in the presence of tetrazole are suitable reagents for the syntheses of oligonucleoside methylphosphonates on a polystyrene support. To test this, the oligomers shown in Table III were prepared. Reactions were carried out in a polypropylene reaction column fitted with a three-way Teflon valve and a septum cap. The reaction cycle is outlined in Table 1 and in the above examples. It was found that one coevaporation with anhydrous pyridine was sufficient to ensure reproducible coupling yields. This was most easily accomplished by placing the entire reaction column in a vacuum bottle containing phosphorous pentoxide and applying a vacuum for 1 hr.

The average yields for the phosphonate coupling steps are shown in Table III. These yields were determined by trityl analysis after each coupling reaction. It was generally observed that a somewhat higher yield was obtained for the initial coupling step (90 to 95%) to form the protected dimer. Subsequent coupling steps remained fairly constant over the range of 3 to 11 nucleoside units. It should be noted that the support remains colorless throughout these phosphonate coupling steps.

In order to simplify the purification procedure and to allow further characterization of the oligomers, the final coupling step involved addition of a protected nucleoside-3-o-chlorophenyl phosphoryl unit. The reaction was carried out in anhydrous pyridine using MSNT as the coupling agent.

Removal of the oligomer from the support and cleavage of the protecting groups was accomplished by the three step procedure previously described (Miller et al, 1983, Nucleic Acid Research, 11, 6225-6242). The o-chlorophenyl protecting group was first removed from the 5'-terminal phosphoriester by treatment with tetra-n-butylammonium fluoride. The oligomer was then removed from the support and the base protecting groups cleaved by treatment with ethanolic ethylenediamine solution. The crude oligomer was examined by reversed phase HPLC.

The dimethoxytrityl group was removed by treatment with 80% acetic acid. The oligomer was positioned by DEAE cellulose chromatography. Since the contaminating oligonucleoside methylphosphonates are unchanged, they pass through the column while the desired oligomer which contains a single phosphodiester group is retained. This oligomer is then eluted from the column with 0.15 M trethylammonium bicarbonate. The overall isolated yield for the oligomer d-CpApTpTpCpTpGpT after DEAE cellulose purification was 47% based on the first nucleoside bound to the polystyrene support.

The foregoing shows that protected deoxynucleoside-3'-methylphosphonic imidazolides are effective and convenient synthetic intermediates for use in the preparation of oligonucleoside methylphosphonates on a polystyrene support. The imidazolides can be prepared directly from commercially available protected nucleosides. The procedure using imidazolides represents a savings in synthetic effort over the previously described procedures which require separate preparation and purification of protected deoxyribonucleoside methyl phosphonates. Since the coupling reactions proceed in relatively high yield with no apparent side reactions, purification of the product is readily achieved by simple ion exchange chromatography. This represents a distinct advantage over the use of preparative reversed phase HPLC where low recoveries of material are sometimes encountered.

Although the syntheses described above were carried out on 70 mg of support, it is evident that the reactions can be directly scaled up to at least 400 mg of support. Thus the present procedure should enable the preparation of relatively large amounts of oligonucleoside methylphosphonates for biochemical or biological studies.

The following Tables I-III are referred to above in discussing the various aspects of the invention:

TABLE I

Reaction Cycle for Preparation of Protected Oligonucleoside Methylphosphonates

| Step | Reagent | Volume | Time |
|---|---|---|---|
| 1. Wash | Methylene chloride/ Isopropanol (85:15 V/V) | 3 × 2 ml | — |
| 2. Detritylation | 1 M zinc bromide in methylene chloride/ isopropanol | 2 × 2 ml (A,G) 4 × 2 ml (T,C) | 4 min each |
| 3. Wash | Methylene chloride/ isopropanol (85:15 V/V) | 3 × 2 ml | |
| 4. Wash | 0.5 M triethylammonium acetate in dimethylformamide | 3 × 2 ml | |
| 5. Wash | Pyridine | 3 × 2 ml | |
| 6. Wash | Ether | 3 × 2 ml | |
| 7. Drying | House vacuum | | 5 min |
| 8. Coevaporation | Add anhydrous pyridine and apply vacuum (oil pump) | 0.42 ml | 60 min |
| 9. Coupling | Protected 5'-Dimethyoxy tityldeoxyribonucleoside-3'-methylphosphonic imidiazolide and tetrazole | 0.3.5 ml | 60 min |
| 10. Wash | Pyridine | 3 × 2 ml | |
| 11. Acetylation | Pyridine/acetic anhydride/dimethylaminopyridine (2 ml, 1 ml, 20 mg) | 3 ml | 10 min |
| 12. Wash | Pyridine | 3 × 2 ml | |

TABLE II

Syntheses of Dinucleoside Methylphosphonates on a Polystyrene Support

| Dimer | Yield[a] |
|---|---|
| d-[(MeO)$_2$Tr]TpT | 99% |
| d-[(MeO)$_2$Tr]CpT | 96% |
| d-[(MeO)$_2$Tr]GpT | 98% |
| d-[(MeO)$_2$Tr]ApT | 98% |

[a]Yields are based on analysis by reversed phase HPLC.

TABLE III

Syntheses of Protected Oligonucleoside Methylphosphonates on a Polystyrene Support

| Protected Oligomer[a] | Average Yield of Phosphonate Coupling Steps[b] |
|---|---|
| d-[(MeO)$_2$Tr]bzCpbzApTpTpbzCpTpibuGpT s | 91% |
| d-[(MeO)$_2$Tr]TpbzCpbzCpTpbzCpbzCpTpibuG s | 83% |
| d-[(MeO)$_2$Tr]bzApTpTpbzApTpbzCpbzCpbzApT s | 85% |

TABLE III-continued

Syntheses of Protected Oligonucleoside
Methylphosphonates on a Polystyrene Support

| Protected Oligomer[a] | Average Yield of Phosphonate Coupling Steps[b] |
|---|---|
| d-[(MeO)$_2$Tr]bzCpbzApTpTpbzCpTpibuGpTpbzCpTpibuGpT s | 87% |

[a]p = methylphosphonate linkage
ṗ = o-chlorophenyl phosphotriester linkage
s = 1% crosslinked polystyrene support
[b]Determined by analysis of the dimethoxytrityl group after each coupling step.

The invention is defined in the following claims wherein:

What is claimed is:

1. A 5'-protected nucleoside-3'-alkyl or arylphosphonic imidazolide or other azole derivative.

2. A product according to claim 1 wherein the alkyl is methyl.

3. A 5'-protected oligonucleoside-3'-alkyl or aryl phosphonate attached to a polymer support.

4. An oligonucleoside according to claim 3 wherein the alkyl is methyl.

5. A process for preparing the nucleoside of claim 1 which comprises reacting a 5'-protected nucleoside with an alkyl or aryl phosphonic-bis-imidazolide or other azole derivative.

6. The process of claim 5 wherein the reaction is carried out in an inert organic solvent.

7. The process of claim 6 wherein the solvent is acetonitrile.

8. The process of claim 5 wherein the imidazolide is methylphosphonic-bis-imidazolide.

9. A process for preparing the oligonucleoside of claim 3 which comprises reacting a 5'-protected nucleoside-3'-alkyl or aryl phosphonic imidazolide or other azole derivative with a nucleoside attached through its 3'-position to a polymer support.

10. The process of claim 9 wherein the 5'-protected position of the product is deprotected and the resulting deprotected product is used as the supported nucleoside for further reaction with a 5'-protected nucleoside-3'-alkyl or arylphosphonic imidazolide, said deprotecting and further reaction being repeated if and as appropriate to provide a final oligomer product of the desired length and composition.

11. The process of claim 10 wherein the final addition step involves reaction with a 5'-protected nucleoside-3'-phosphate derivative to provide a final oligomer product of the desired length which terminates with a 5'-nucleotide group.

12. A process according to claim 9 wherein the reaction is carried out in the presence of tetrazole or other azole derivative as catalyst.

13. A process according to claim 9 wherein the product is deprotected and removed from the support by treatment with fluoride, ethylene diamine and acetic acid.

14. A process according to claim 13 wherein the deprotected product removed from the support is purified by ion exchange chromatography.

* * * * *